United States Patent [19]

Ackerman et al.

[11] Patent Number: 5,102,883

[45] Date of Patent: Apr. 7, 1992

[54] PYRIMIDINE BIOSYNTHESIS INHIBITORS USEFUL AS IMMUNOSUPPRESSIVE AGENTS

[75] Inventors: Neil R. Ackerman, Greenville; Bruce D. Jaffee, Wilmington, both of Del.

[73] Assignee: Du Pont Merck Pharmaceutical Company, Wilmington, Del.

[21] Appl. No.: 430,891

[22] Filed: Oct. 31, 1989

[51] Int. Cl.$^5$ .................. A61K 31/41; A61K 9/00; C07K 17/02; G01N 33/544

[52] U.S. Cl. ................................. 514/23; 514/903; 536/53; 536/55

[58] Field of Search ............... 514/23, 903; 536/53, 536/55

[56]  References Cited

U.S. PATENT DOCUMENTS

| | | | |
|---|---|---|---|
| 3,509,208 | 4/1970 | Alburn et al. | 514/814 |
| 3,802,999 | 4/1974 | Williams et al. | 435/118 |
| 3,960,836 | 6/1976 | Gatowski | 536/53 |
| 3,998,999 | 12/1976 | DeBernardo et al. | 536/55 |
| 4,154,759 | 5/1979 | Parsons | 562/15 |
| 4,178,306 | 12/1979 | Parsons | 562/15 |
| 4,179,464 | 12/1979 | Schultz et al. | 562/15 |
| 4,215,070 | 7/1980 | Schultz et al. | 562/15 |
| 4,267,126 | 5/1981 | Schultz et al. | 558/174 |
| 4,680,299 | 7/1987 | Hesson | 514/311 |
| 4,861,783 | 8/1989 | Ackerman et al. | 514/861 |
| 4,904,481 | 2/1990 | Fathman | 514/885 |
| 4,950,687 | 8/1990 | Dall'Asta et al. | 514/903 |
| 4,968,701 | 11/1990 | Ackerman et al. | 514/312 |
| 4,994,442 | 2/1991 | Gil et al. | 514/885 |
| 4,994,466 | 2/1991 | Sherman et al. | 514/903 |

FOREIGN PATENT DOCUMENTS 184040  6/1986  European Pat. Off. .

OTHER PUBLICATIONS

Shih-Fong Chen et al., Cancer Research 46, 5014–5019, Oct. 1989.

Primary Examiner—Ronald W. Griffin
Attorney, Agent, or Firm—Blair Q. Ferguson

[57]  ABSTRACT

The pyrimidine biosynthesis inhibitors dichloroallyl lawsone, N-(phosphonoacetyl)-L-aspartic acid (PALA), pyrazofurin, and derivatives thereof, are useful as immunomodulatory and anti-inflammatory agents. Pharmaceutical formulations containing these compounds are useful for the treatment of autoimmune diseases, chronic inflammatory diseases, and of organ transplantation rejections.

2 Claims, No Drawings

PYRIMIDINE BIOSYNTHESIS INHIBITORS USEFUL AS IMMUNOSUPPRESSIVE AGENTS

BACKGROUND OF THE INVENTION

1. Field of Invention

This invention relates to methods of treating autoimmune and chronic inflammatory diseases, and organ transplantation rejections and more particularly to such methods using pyrimidine biosynthesis inhibitors.

2. Prior Art

A dysfunction of the immune system can manifest itself as an autoimmune disease such as multiple sclerosis, rheumatoid arthritis, systemic lupus erythematous, and the like, and chronic inflammatory diseases. Organ transplantation rejection may also be an immune-based inflammatory response. Agents which have an immunosuppressive effect would be highly desirable for the treatment of these diseases.

3. Information Disclosure

Dichloroallyl lawsone is an anticancer drug which is described in U.S. Pat. No. 3,655,699, granted Apr. 11, 1972, to H. Putner.

Pyrazofurin and pyrazofurin B are antibiotics having antiviral and antifungal activity. These compounds, their alkanoyl derivatives, and their preparation are described in U.S. Pat. No. 3,802,999, granted Apr. 9, 1974, to Williams et al.; U.S. Pat. No. 3,998,999, granted Dec. 21, 1976, to De Bernardo et al.; and U.S. Pat. No. 3,960,836, granted June 1, 1976, to Gatowski.

N-(phosphonoacetyl)-L-aspartic acid (PALA) and its analogs are compounds useful for the treatment of cancer. These compounds, intermediates thereto and their preparation are described in U.S. Pat. No. 4,267,126, granted May 12, 1981, to Schultz et al.; U.S. Pat. No. 4,215,070, granted July 29, 1980, to Schultz et al.; U.S. Pat. No. 4,179,464, granted Dec. 18, 1979, to Schultz et al., U.S. Pat. No. 4,154,759, granted May 15, 1979, to Parsons; and U.S. Pat. No. 4,178,306, granted Dec. 11, 1979, to Parsons.

SUMMARY OF THE INVENTION

According to the present invention there is provided a method of treating an autoimmune disease, a chronic inflammatory disease, or organ transplantation rejection in a mammal comprising administering to the mammal an effective amount of a pyrimidine biosynthesis inhibitor selected from the group consisting of:

(a) a compound of the formula:

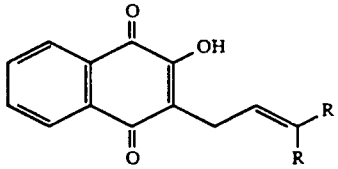

wherein each R is $CF_3$ or halogen;

(b) a compound of the formula

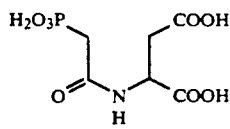

or a pharmaceutically acceptable salt thereof, or dialkyl ($C_1$-$C_4$) or dibenzyl ester thereof; and (c) pyrazofurin of the formula:

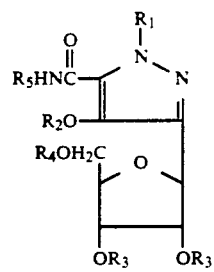

where $R_1$, $R_2$, and $R_3$ and $R_5$ independently are H or $C_1$-$C_6$ alkanoyl and $R_4$ is H, $C_1$-$C_6$ alkanoyl, palmitoyl, benzoyl, or adamantoyl.

DETAILED DESCRIPTION OF THE INVENTION

The compounds useful in the method of this invention are known compounds described in the U.S. patents set forth in the Information Disclosure section, supra. The disclosures in these patents to the compounds and their preparation are hereby incorporated by reference.

Preferred compounds are (1) those of formula (a) wherein each R is halogen, particularly Cl; (2) those of formula (b) wherein a salt of the compound is used, particularly an alkali metal salt; and (3) those of formula (c) wherein each of $R_1$-$R_5$ is H.

The specifically preferred compounds useful in the present method are dichloroallyl lawsone, PALA, disodium salt and pyrazofurin. These are specific compounds described in the aforesaid patents.

The invention can be further understood by the following examples in which parts and percentages are by weight unless otherwise indicated.

Human Mixed Lymphocyte Reaction

Blood was obtained by venipuncture from two non-related human donors. Peripheral blood mononuclear cells (PBMC) were isolated from these samples by using the Leuco Prep procedure (Becton-Dickinson). PBMC were washed twice in phosphate buffered saline (without calcium and magnesium) and the separate cell isolations were adjusted to the appropriate concentrations in media (RPMI 1640) supplemented with 10% human AB serum and 50 ul/ml gentamicin. Cells from donor A ($2 \times 10^5$) were incubated with cells from donor B ($2 \times 10^5$) with or without compound in 96 well round bottom microtiter plates at 37° C., 5% $CO_2$ for 6 days. Eighteen hours prior to harvesting cells from the plates, all wells were pulsed with 1 uCi of tritiated-thymidine. Cells from the plates were harvested on day 6 and tritiated-thymidine incorporation was determined using a scintillation counter. Test results are shown in the following table.

| COMPOUND | IC50 (M) |
| --- | --- |
| Pyrazofurin | $8.0 \times 10^{-9}$ |
| Dichloroallyl Lawsone | $4.5 \times 10^{-6}$ |
| PALA | $4.5 \times 10^{-5}$ |

The test results show that these compounds suppress an in vitro immune response. Based on these data, the compounds useful in this invention should be efficacious in treating autoimmune diseases, multiple sclerosis and chronic inflammatory diseases such as rheumatoid arthritis; all of which involve T lymphocyte mediated components. Activities in the human mixed lymphocyte reaction indicate that the compounds useful in the invention should be effective in preventing transplantation rejection and graft vs. host disease.

DOSAGE FORMS

The useful compounds (active ingredients) of this invention can be administered by any means that produces contact of the active ingredient with the agent's site of action in the body of a mammal. They can be administered by any conventional means available for use in conjunction with pharmaceuticals; either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be an effective amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired Usually a daily dosage of active ingredient per kilogram of body weight. Ordinarily 1 to 100, and preferably 10 to 50 milligrams per kilogram per day is effective to obtain desired results.

Dosage forms (compositions) suitable for internal administration contain from about 10-500 milligrams to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), an related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

CAPSULES

A large number of unit capsules are prepared by filling standard two-piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is made isotonic with sodium chloride and sterilized.

SUSPENSION

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs. Suitable dosages, dosage forms and administration routes are illustrated in the following table.

Examples of NSAID's that can be combined with the compounds used in this invention:

| Drug | Dose (mg) | Formulation | Route |
|---|---|---|---|
| Indomethacin | 25 (2/3 times daily) | Tablet | Oral |
| Meclofenamate | 50-100 | Tablet | Oral |

| Drug | Dose (mg) | Formulation | Route |
|---|---|---|---|
| Ibuprofen | (2/3 times daily) 300–400 | Tablet | Oral |
| Piroxicam | (3/4 times daily) 10–20 | Tablet | Oral |
| Sulindac | (1/2 times daily) 150–200 | Tablet | Oral |
| Azapropazone | (1/2 times daily) 200–500 (3/4 times daily) | Tablet | Oral |

What is claimed is:

1. A method of treating an autoimmune disease, a chronic inflammatory disease, or organ transplantation rejection in a mammal comprising administering to the mammal an effective amount of a pyrimidine biosynethesis inhibitor selected from the group consisting of: pyrozofurin and acylated derivatives thereof of the formula:

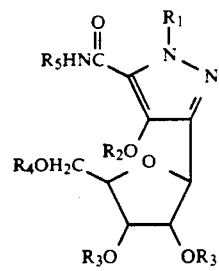

where $R_1$, $R_2$, $R_3$ and $R_5$ independently are H or $C_1$–$C_6$ alkanoyl and $R_4$ is H, $C_1$–$C_6$ alkanoyl, palmitoyl, benzoyl, or adamantoyl.

2. The method of claim 1 wherein the compound is pyrazofurin.